(12) United States Patent
Schoon

(10) Patent No.: US 6,319,280 B1
(45) Date of Patent: Nov. 20, 2001

(54) PROSTHETIC RING HOLDER

(75) Inventor: Thomas G. Schoon, Cedar, MN (US)

(73) Assignee: St. Jude Medical, Inc., St. Paul, MN (US)

( * ) Notice: Subject to any disclaimer, the term of this patent is extended or adjusted under 35 U.S.C. 154(b) by 0 days.

(21) Appl. No.: 09/366,518

(22) Filed: Aug. 3, 1999

(51) Int. Cl.$^7$ ........................................... A61F 2/24
(52) U.S. Cl. ........................ 623/2.11; 623/900; 606/1
(58) Field of Search ........................ 623/2.11, 2.1, 623/900; 606/1

(56) References Cited

U.S. PATENT DOCUMENTS

| | | | |
|---|---|---|---|
| 3,546,710 | 12/1970 | Shumakov et al. | 3/1 |
| 3,574,865 | 4/1971 | Hamaker | 3/1 |
| 3,625,220 | 12/1971 | Engelsher | 128/335 |
| 3,691,567 | 9/1972 | Cromie | 3/1 |
| 3,828,787 | 8/1974 | Anderson et al. | 128/303 |
| 3,996,623 | 12/1976 | Kaster | 3/1 |
| 4,009,719 | 3/1977 | Kletschka et al. | 128/335 |
| 4,055,861 | 11/1977 | Carpentier et al. | 3/1.5 |
| 4,084,268 | 4/1978 | Ionescu et al. | 3/1.5 |
| 4,172,295 | 10/1979 | Batten | 3/1.5 |
| 4,233,690 | 11/1980 | Akins | 3/1.5 |
| 4,290,151 | 9/1981 | Massana | 3/1.5 |
| 4,388,735 | 6/1983 | Ionescu et al. | 3/1.5 |
| 4,585,453 | 4/1986 | Martin et al. | 623/2 |
| 4,585,458 | 4/1986 | Kurland | 623/13 |
| 4,612,011 | 9/1986 | Kautzky | 623/2 |
| 4,629,459 | 12/1986 | Ionescu et al. | 623/2 |
| 4,665,906 | 5/1987 | Jervis | 128/92 |
| 4,679,556 | 7/1987 | Lubock et al. | 128/303 |
| 4,683,883 * | 8/1987 | Martin | 128/303 |
| 4,865,600 | 9/1989 | Carpentier et al. | 623/2 |
| 4,907,590 | 3/1990 | Wang et al. | 606/139 |
| 4,987,904 | 1/1991 | Wilson | 128/774 |
| 5,011,481 | 4/1991 | Myers et al. | 606/1 |
| 5,041,130 | 8/1991 | Cosgrove et al. | 623/2 |
| 5,061,277 | 10/1991 | Carpentier et al. | 623/2 |
| 5,064,431 | 11/1991 | Gilbertson et al. | 623/2 |
| 5,104,407 | 4/1992 | Lam et al. | 623/2 |
| 5,197,979 | 3/1993 | Quintero et al. | 623/2 |
| 5,236,450 * | 8/1993 | Scott | 623/2 |
| 5,290,300 | 3/1994 | Cosgrove et al. | 606/148 |
| 5,326,371 | 7/1994 | Love et al. | 623/2 |
| 5,336,258 | 8/1994 | Quintero et al. | 623/2 |
| 5,350,420 * | 9/1994 | Cosgrove et al. | 623/2 |
| 5,360,014 | 11/1994 | Sauter et al. | 128/774 |

(List continued on next page.)

FOREIGN PATENT DOCUMENTS

| | | |
|---|---|---|
| 1 180 087 | 10/1964 | (DE) . |
| WO 96/39942 | 12/1996 | (WO) . |
| WO 89/00841 | 2/1998 | (WO) . |
| WO 98/49974 | 11/1998 | (WO) . |

OTHER PUBLICATIONS

"Prosthetic Rings and Accessories for Tricuspid and Mitral Valvuloplasty", *Carpentier–Edward®*, Dec. 1985, pp. 1–8.
"Techniques for Implanting the SMJ® Séguin Annuloplasty Ring for Mitral Valve Repair", *St. Jude Medical*, 1996, 4 pages.

Primary Examiner—David J. Isabella
Assistant Examiner—Urmi Chattopadhyay
(74) Attorney, Agent, or Firm—Hallie A. Finucane, Esq.; Westman, Champlin & Kelly, P.A.

(57) ABSTRACT

A holder is provided for carrying a prosthetic ring which allows for manipulation and handling of the ring during implantation in a heart. The holder includes a holder body configured to fit the ring. A boss extends around the holder body. A backing lip extends from a proximal end of the boss and has a diameter that is greater than a diameter of the boss. A shoulder tab extends only partially around the distal end of the boss and extends beyond a diameter of the boss. The prosthetic ring mates with the boss and the backing lip to thereby hold the prosthetic ring.

20 Claims, 11 Drawing Sheets

U.S. PATENT DOCUMENTS

| | | | |
|---|---|---|---|
| 5,403,305 | 4/1995 | Sauter et al. | 606/1 |
| 5,415,667 | 5/1995 | Frater | 623/2 |
| 5,443,502 * | 8/1995 | Caudillo et al. | 623/2 |
| 5,471,756 | 12/1995 | Bolanos et al. | 33/501.45 |
| 5,489,296 | 2/1996 | Love et al. | 623/2 |
| 5,522,884 | 6/1996 | Wright | 623/2 |
| 5,571,175 | 11/1996 | Vanney et al. | 623/2 |
| 5,578,076 | 11/1996 | Krueger et al. | 623/2 |
| 5,669,919 | 9/1997 | Sanders et al. | 606/148 |
| 5,766,240 | 6/1998 | Johnson | 623/2 |
| 5,776,187 * | 7/1998 | Krueger et al. | 623/2 |
| 5,776,188 | 7/1998 | Shepherd et al. | 623/2 |
| 5,776,189 | 7/1998 | Khalid | 623/2 |
| 5,824,066 | 10/1998 | Gross | 623/2 |
| 5,824,069 | 10/1998 | Lemole | 623/2 |
| 5,843,177 | 12/1998 | Vanney et al. | 623/2 |
| 5,906,642 | 5/1999 | Caudillo et al. | 623/2 |

* cited by examiner

PROSTHETIC RING HOLDER

FIELD OF THE INVENTION

The present invention relates to prosthetic heart implants of the type which include a prosthetic ring. More specifically, the invention relates to a holder for a prosthetic heart ring.

BACKGROUND OF THE INVENTION

Prosthetic heart implants are devices used to repair or assist hearts which have been damaged through diseases or other defects. One type of prosthetic heart implant is a prosthetic heart valve. Another type of prosthetic implant is an annuloplasty ring. Prosthetic heart valves are used to replace a damaged natural heart valve. Annuloplasty rings are used to repair a natural heart valve which has been damaged due to certain types of diseases or defects which reduce the efficiency of the valve. For example, the radius of the valve can become enlarged or deformed such that the cusps of the natural valve do not form a seal when the valve is in a closed position.

Both of these prosthetic heart devices include a prosthetic ring which is implanted into the heart. During the implantation procedure, the prosthetic device must be held in a manner such that it may be manipulated by a surgeon. Typically, some type of holder is used for the manipulation. For example, U.S. Pat. No. 5,578,076 shows a holder for a prosthetic heart valve. Similarly, U.S. Pat. Nos. 5,041,130 and 5,011,481 show holders for use with annuloplasty rings.

SUMMARY OF THE INVENTION

An apparatus for attaching to a prosthetic ring for implantation in a heart includes a holder body configured to fit in the ring. A boss in the holder body includes at least a partial generally cylindrical portion extending around the holder body. A backing lip in the holder body extends from a first end of the boss and has a diameter which is greater than a diameter of the boss. A shoulder tab extends beyond a diameter of the boss proximate a second end of the boss and is adapted to secure the prosthetic ring between the backing lip and the shoulder tab.

DETAILED DESCRIPTION OF THE PREFERRED EMBODIMENTS

The present invention provides an apparatus or holder for attaching or holding a prosthetic ring, such as a prosthetic heart valve or an annuloplasty ring. The apparatus can be used with conventional heart valves or the outer ring of two piece heart valves, such as that shown in commonly assigned U.S. application Ser. No. 09/062,822 and with two piece heart valves. The holder of the present invention is easily removed from the prosthetic ring during the implantation process. Further, the design of the holder allows the holder to be easily repositioned to subsequently rotate the prosthetic valve mechanism.

Figure 1A:
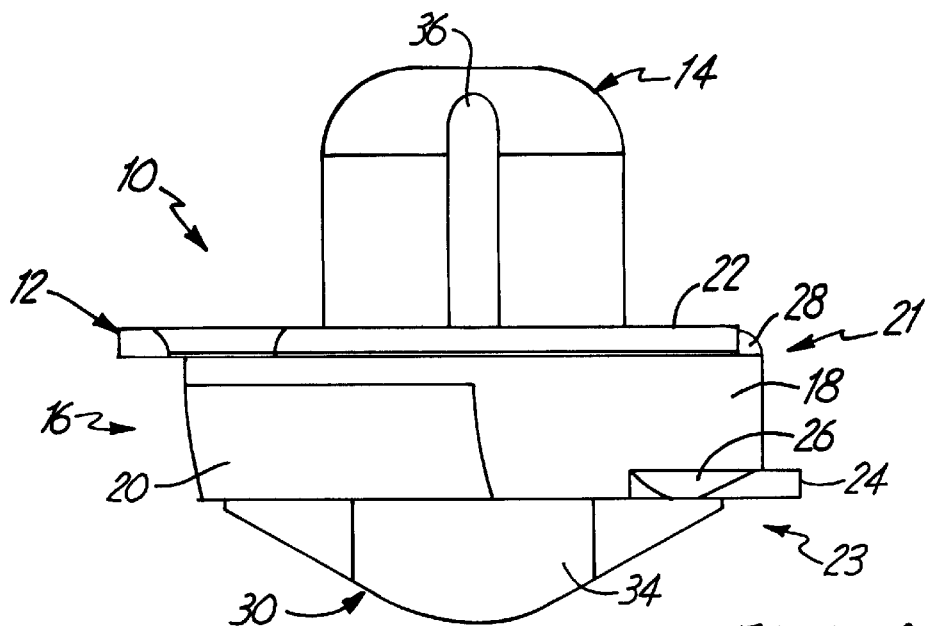
FIG. 1A is a side plan view of a prosthetic ring holder in accordance with the present invention.
Figure 1B:
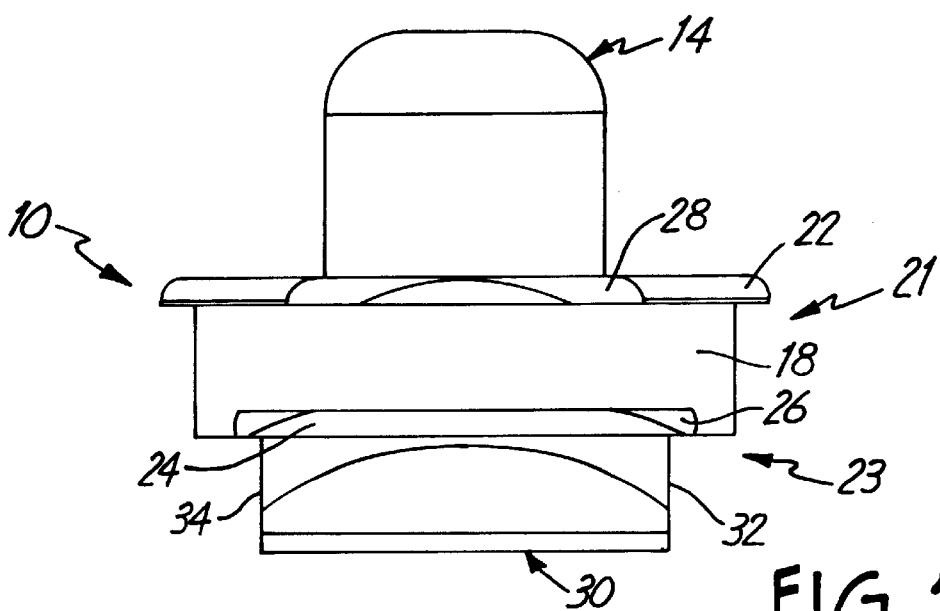
FIG. 1B is another side plan view of the prosthetic ring holder.

FIGS. 1A and 1B are side plan views of a prosthetic ring holder 10 in accordance with one embodiment of the present invention. Holder 10 is preferably fabricated using a mold. Prosthetic ring holder 10 includes a holder body 12 having a handle attachment portion 14, a ring attachment portion 16, and a valve rotation portion 30.

Ring attachment portion 16 includes a boss 18 which has at least a partial generally cylindrical portion. Boss 18 includes a relief area 20 formed therein, such that material is removed (cut away) from the cylindrical surface of boss 18 to form a spherical surface of relief area 20. A backing lip 22 has a diameter which is greater than the diameter of boss 18 and is positioned on a proximal end 21 of boss 18. A shoulder tab 24 has a diameter which is greater than a diameter of boss 18 and is positioned on a distal end 23 of boss 18. Tab 24 extends only partially around the circumference of boss 18. In one preferred embodiment, tab 24 extends between about 45 and about 135 degrees around the circumference of boss 18. Tab 24 includes a relief region 26 formed therein such that material is removed (cut away) to form a complex curved surface in relief region 26. Backing lip 22 includes a relief region 28 formed therein formed from material that is removed (cut away) in a straight line cut of backing lip 22 and blended with the body of boss 18.

Ring attachment portion 16 further includes an optional prosthetic heart valve rotation portion 30 having orifice engaging surfaces 32 and 34 used as the rotation mechanism. Valve rotation portion 30 is not required for use with many ring prosthetics, such as an annuloplasty ring. In most applications, rotation portion 30 can be included with holder 10 such as when holding a conventional mechanical or a two piece mechanical heart valve. Portion 30 can be configured to mate with any type of heart valve. For example, several configurations are illustrated in U.S. Pat. No. 5,776,187, issued Jul. 7, 1998.

Figure 2:
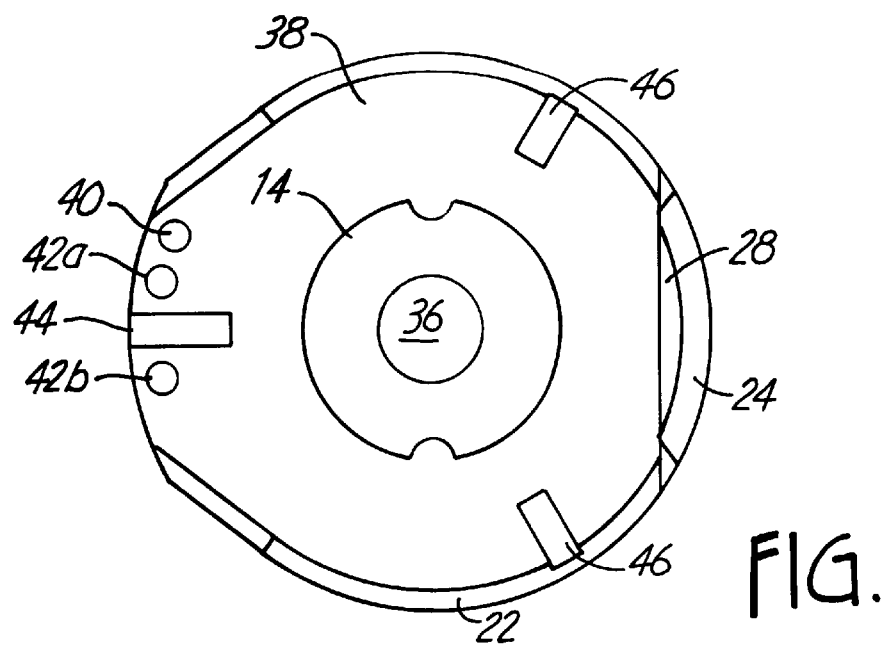
FIG. 2 is a top plan view of the prosthetic ring holder of FIGS. 1A and 1B.

FIG. 2 is a top plan view of holder 10 showing handle attachment portion 14, a top surface 38, backing lip 22 and shoulder tab 24 which is visible through relief area 28. Suture holes 40 and 42a,b are formed in surface 38 generally opposite relief region 28. Further, a marker and channel region 44 is positioned between suture holes 42a,b. Suture markers 46 are also positioned on surface 38 to aid in alignment of prosthetic ring during implantation. The number of suture markers 46 can vary, depending if for aortic or mitral applications.

Figure 3:
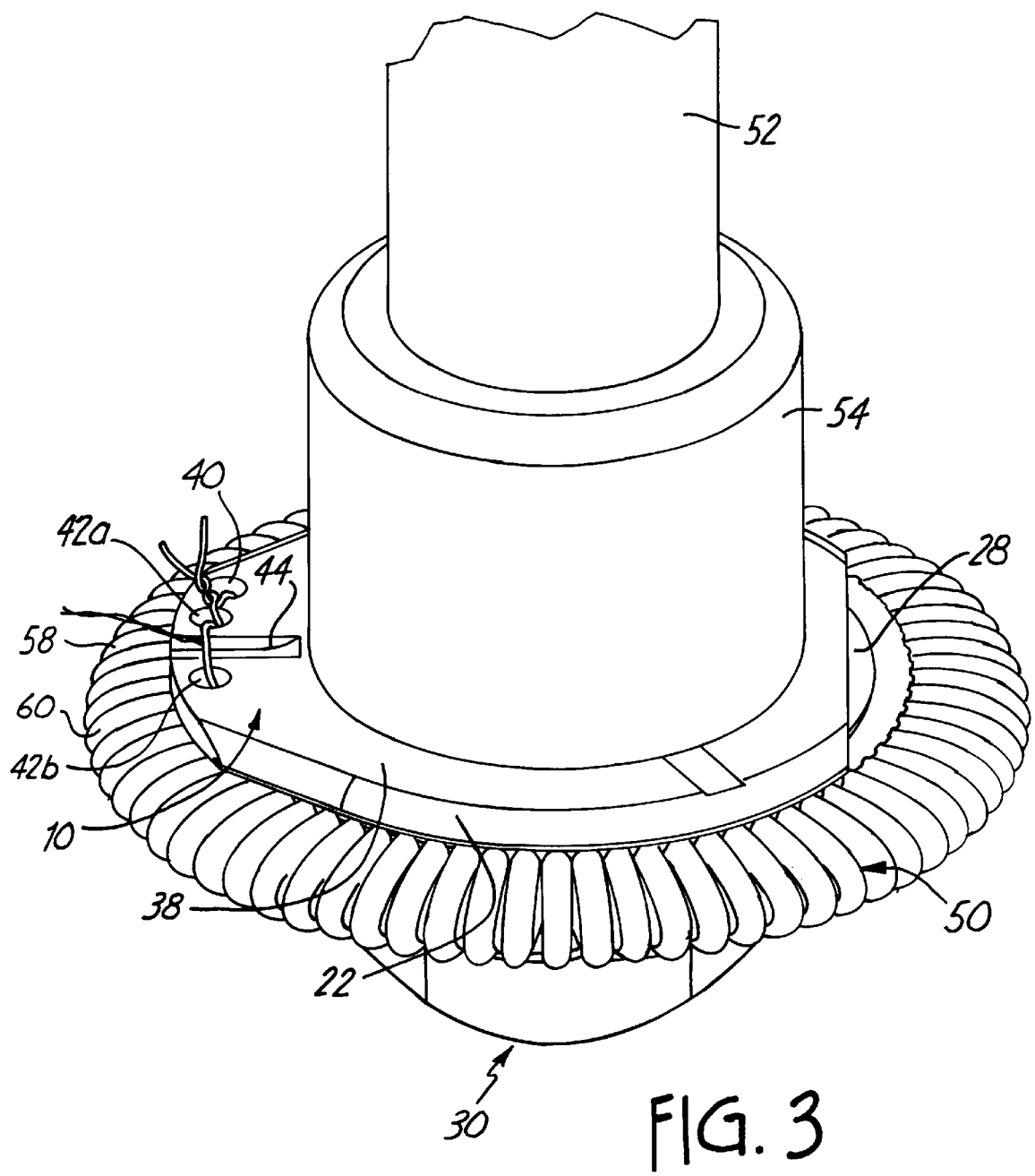
FIGS. 3 and 4 are perspective views showing a prosthetic ring holder coupled to a prosthetic ring.

FIG. 3 is a perspective view of holder 10 coupled to prosthetic ring 50 and held by handle 52 through connector 54. A suture 58 extends through suture holes 42a and 42b into cuff 60 of prosthetic ring 50. Holes 40 and 42a are provided for tying knots to retain or keep suture 58 with holder 10 when holder 10 is removed. A portion of suture 58 extends over channel region 44. This portion of suture 58 is cut to remove holder 10 from prosthetic ring 50 as described below. Prosthetic ring 50 is shown for illustrative purposes only and may comprise any ring configuration for implantation in a heart. Prosthetic ring 50 may be an annuloplasty ring, the annulus of a prosthetic heart valve or other rigid or semi-rigid rings. In the configuration shown in FIGS. 3–5, prosthetic ring 50 is securely held to holder 10 at two locations approximately 180° apart by suture 58 extending between holes 42a,42b and between backing lip 22 and shoulder tab 24 (shown in FIG. 5).

Figure 4:
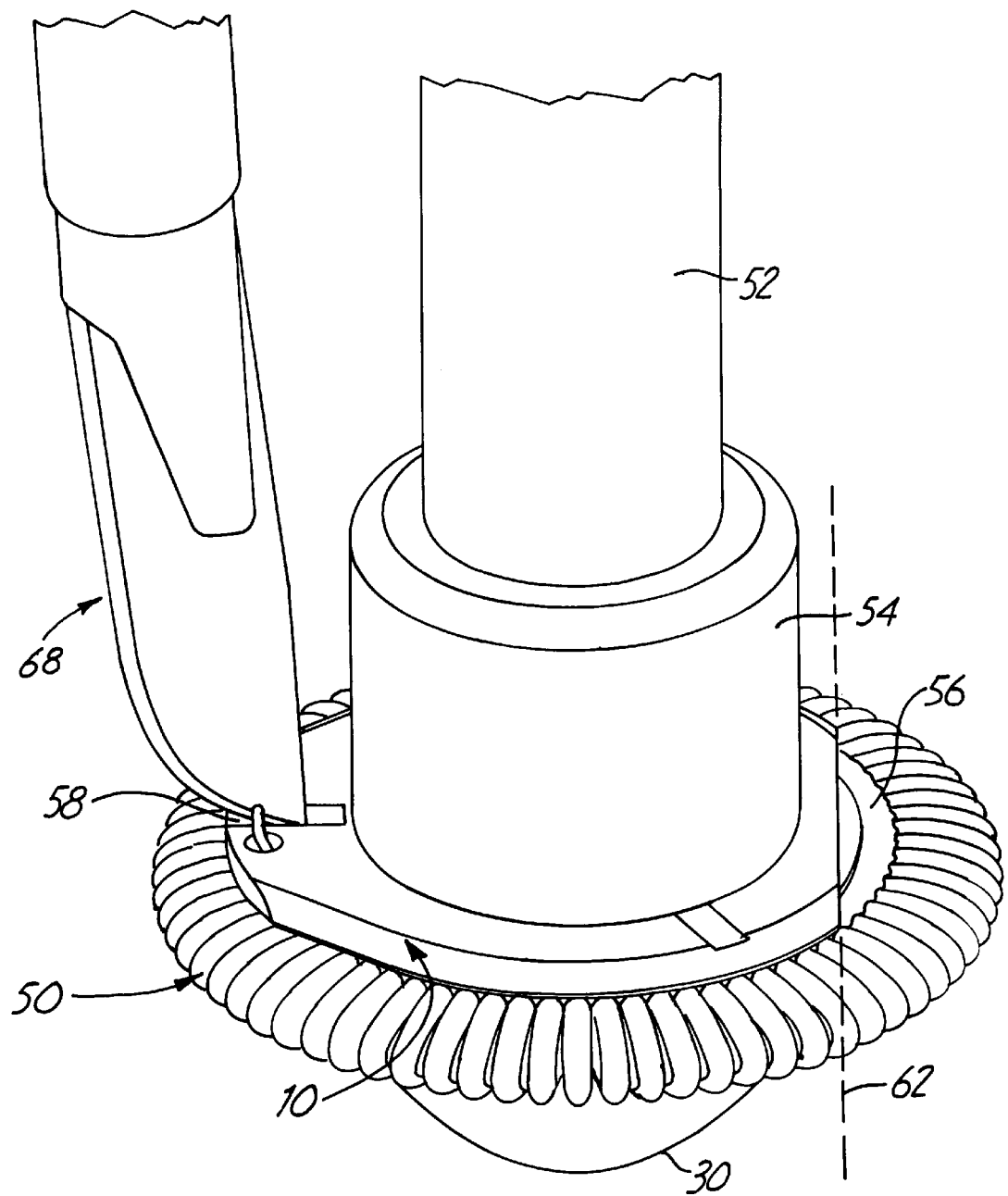
Figure 5A:
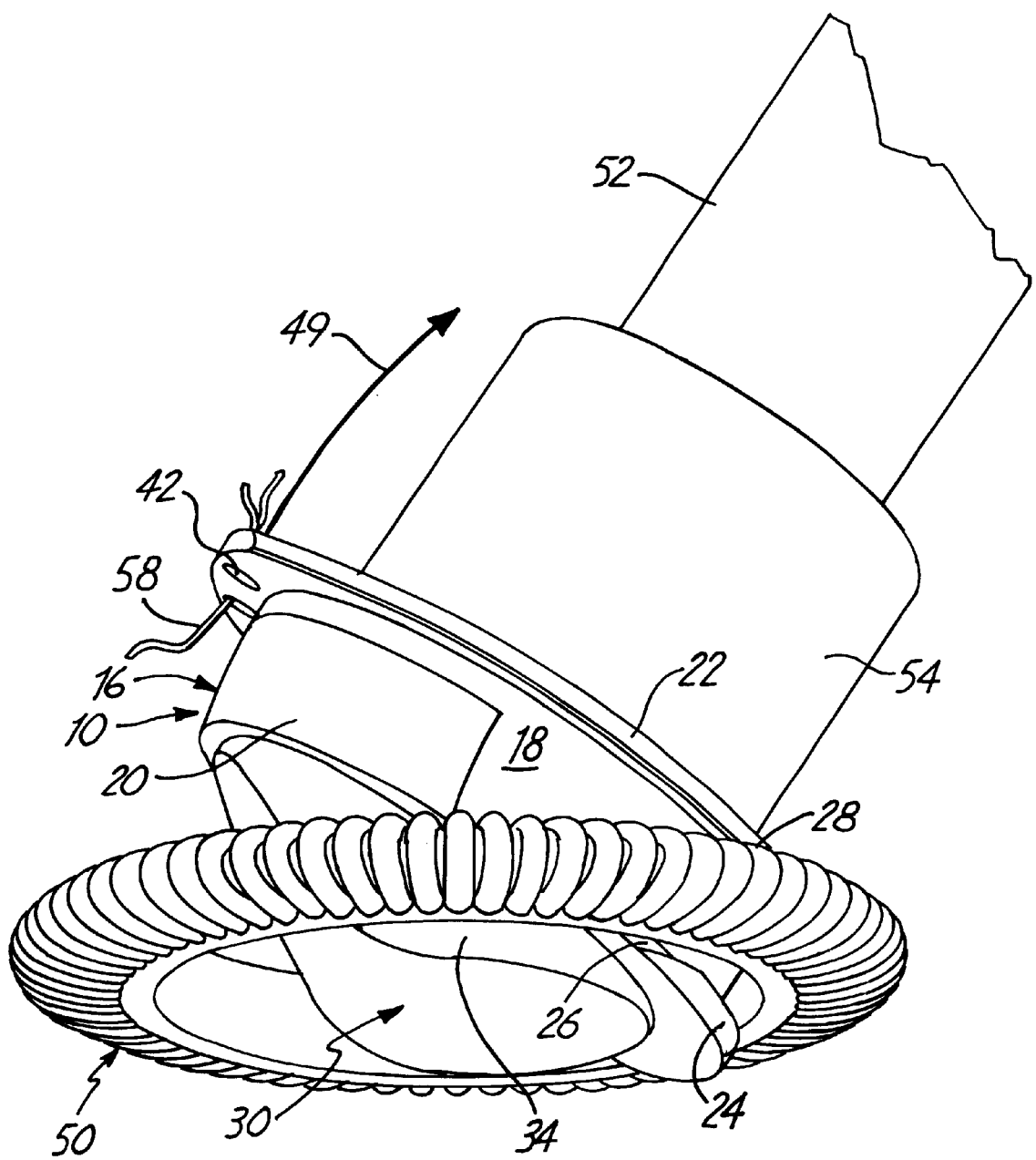
FIG. 5A is a perspective view showing the prosthetic ring holder being removed from the prosthetic ring and FIG. 5B is a cross-section of the holder being reinserted to rotate valve after ring has been sutured into position and the valve has been assembled into the ring.

Using handle 52, a surgeon can manipulate prosthetic ring 50 and position prosthetic ring 50 within a patient's heart. After cuff 60 has been sutured to the tissue annulus of the patient, suture 58 can be cut at channel region 44 using a scalpel 68, as illustrated in FIG. 4. After suture 58 is severed, holder 10 can be tilted or lifted with a slight rotation along pivot line 62, thereby pivoting against the top surface 56 of ring 50 as illustrated in the perspective view of FIGS. 4 and 5A and thereby removing the holder from prosthetic ring 50. Relief areas 20, 26 and 28 are formed to allow the tilting along trajectory 49 illustrated in FIG. 5A such that holder 10 can pivot about pivot line 62 and be removed from prosthetic ring 50 in a smooth frictionless arc.

Figure 5B:
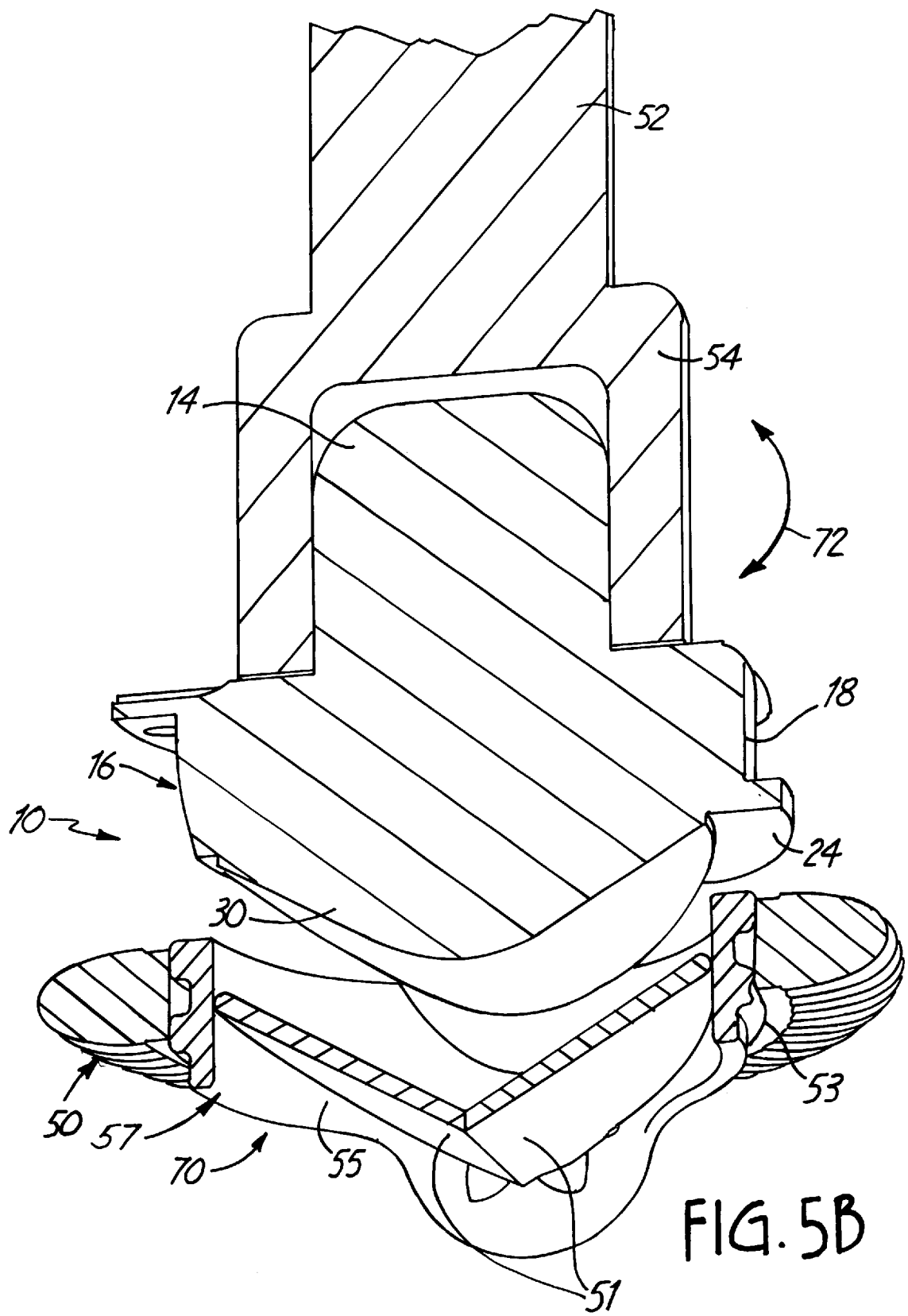

If prosthetic ring 50 is the outer ring or annulus of a two-piece prosthetic heart valve as shown in FIG. 5B, then after removal of holder 10 the surgeon inserts the orifice 55 and leaflets or occluders 51 of subassembly 57 into ring 50, completing assembly of the mechanical heart valve 70. If the surgeon observes that there is blockage of the leaflet 51, holder 10 can be reinserted into the prosthetic heart valve orifice 55 as shown in FIG. 5B and used to rotate subassembly 57 of the prosthetic heart valve 70, pivoting on diameter 53 as described in U.S. Pat. No. 5,776,187, issued Jul. 7, 1998. This allows the surgeon to achieve the desired orientation of the prosthetic heart valve after suturing the ring 50 to the natural tissue annulus. When used to rotate a heart valve, the holder body is configured to transmit a torque 72 to a mechanical heart valve. FIG. 5B also shows the relationship between rotation portion 30 and leaflets 51 of valve 50.

Figure 6:
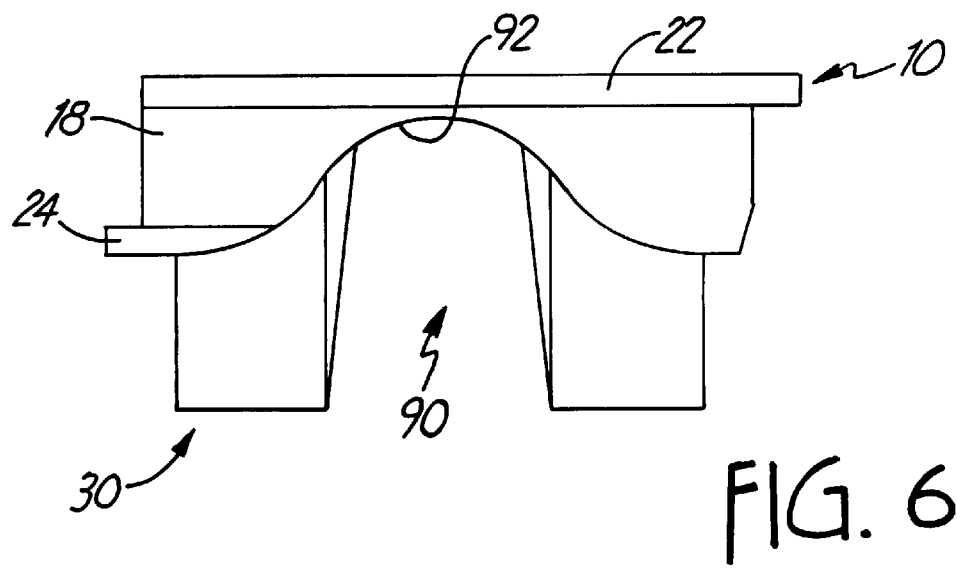
FIG. 6 is a side plan view of a prosthetic ring holder in accordance with another embodiment.

Optional valve rotation portion 30 can be configured to mate with either a mitral or aortic (see FIGS. 1–5) prosthetic heart valve. FIG. 6 is a side plan view of holder 10 including valve rotation portion 30 configured to couple to a two-piece mitral valve. Ring 50 fits on boss 18 for holding ring 50 during implantation. If rotation of a heart valve is desired after the implantation, valve rotation portion 30 would be inserted into the orifice 55 of the heart valve, such that shoulder tab 24 would rest on the top (distal) rim or surface of the valve orifice 55. Rotation portion 30 includes leaflet recess area 90 and orifice engaging surfaces 92 which makes the holder specifically adapted to fit a mitral rotatable valve available from St. Jude Medical, Inc. of St. Paul, Minn. However, the holder can be modified to mate with other valve configurations.

Figure 7A:
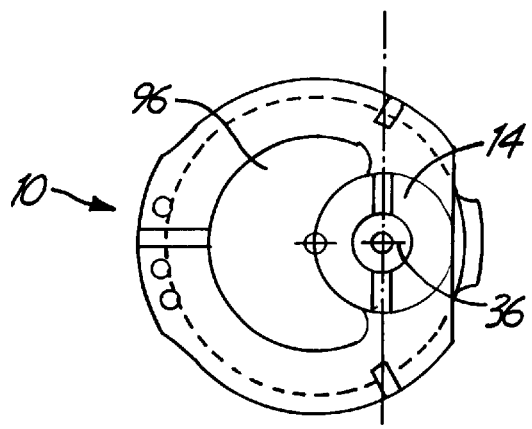
FIGS. 7A, 7B, 7C and 7D are top plan views showing various embodiments of prosthetic ring holders in accordance with the invention.
Figure 7B:
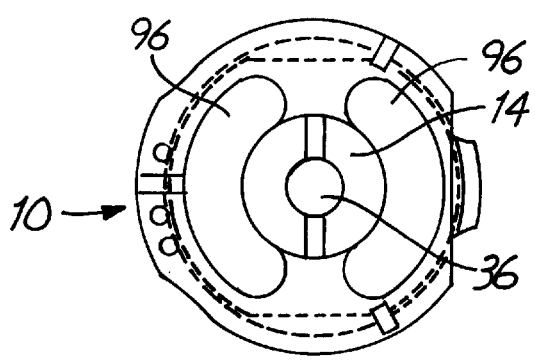
Figure 7C:
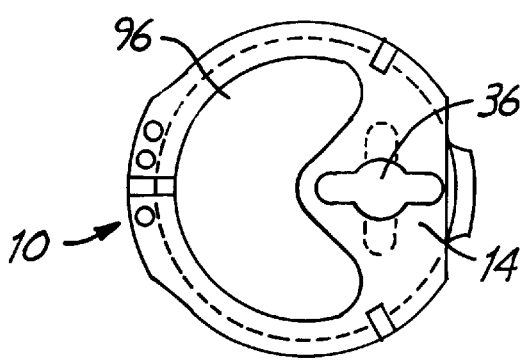
Figure 7D:
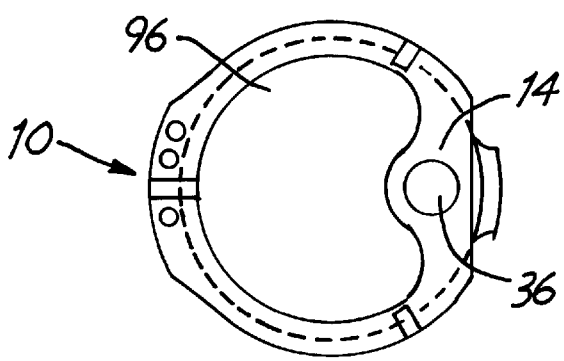

Handle attachment portion 14 includes handle opening 36 formed therein. The handle and the handle attachment portion 14 can be of any configuration as is known in the art. For example, the handle 52 shown in FIGS. 3, 4 and 5A,B can be coupled to holder 10 by a press fit whereby the connector 54 of handle 52 is adapted to be pressed over handle attachment portion 14. Handle attachment portion 14 can also be used to support holder and the prosthetic ring in packaging during shipping. The handle attachment portion 14 can be positioned in the center of holder 10, or positioned offset from the center to allow improved visual inspection during implantation. FIGS. 7A, 7B, 7C and 7D are top plan views showing various configurations of holder 10. The FIGS. 7 show various locations of handle attachment portion 14 and cutout regions 96. Cutout regions 96, which may be optional, allow improved visual inspection during implantation. In FIGS. 7A and 7B, handle attachment portion 14 is configured to receive a snap fit handle. In FIG. 7C, handle attachment portion 14 is configured to receive a spring-loaded twist lock handle as described in U.S. Pat. No. 5,843,177. In FIG. 7D, handle attachment portion 14 is configured to receive a threaded handle.

Figure 8:
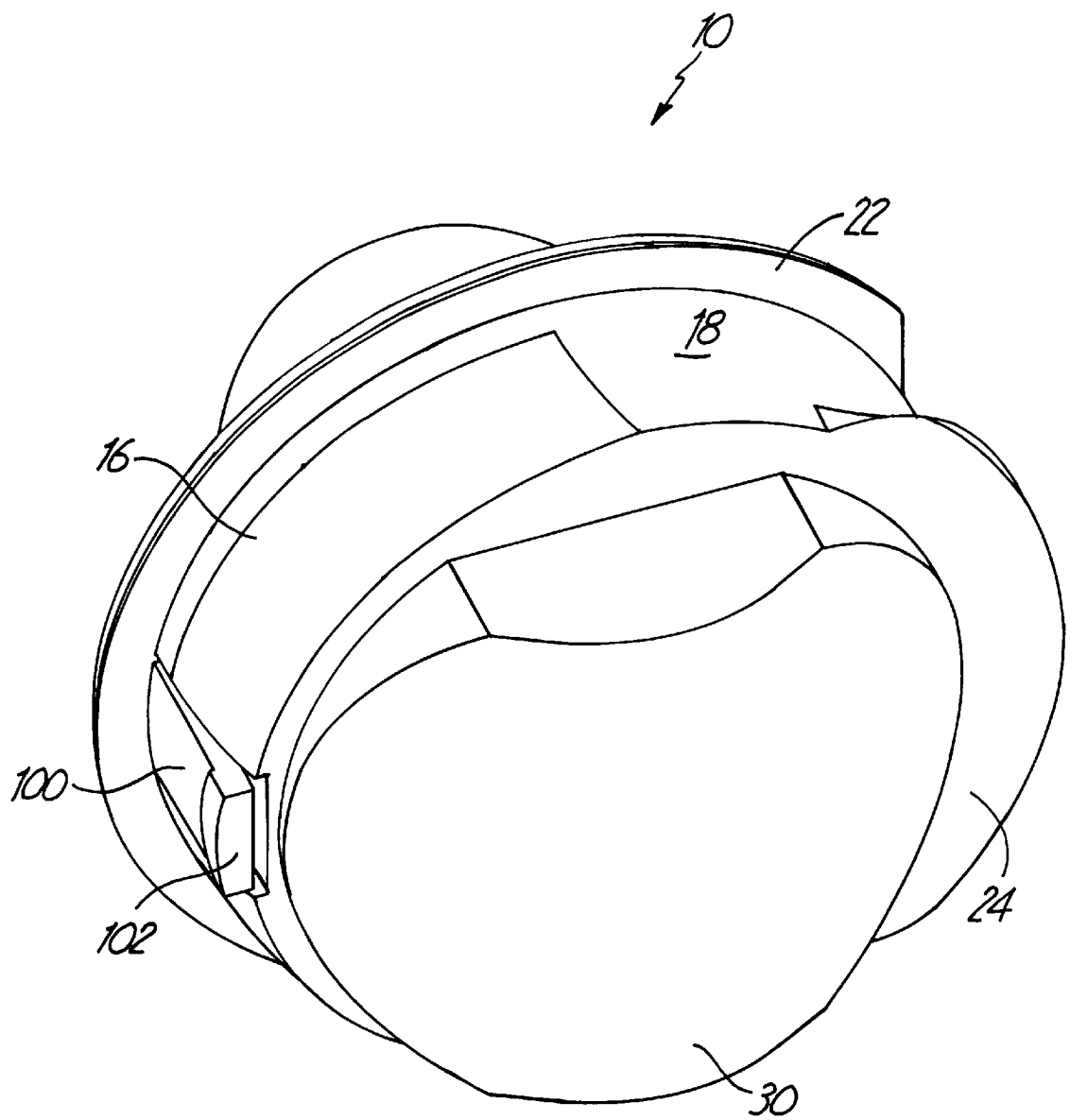
FIG. 8 is a bottom perspective view of holder in accordance with another embodiment.

FIG. 8 is a bottom plan view of another embodiment of holder 10 which includes flexible tab 100 having ring retaining lip 102. In this embodiment, holder 10 can be secured to ring 50 using tab 100 such that lip 102 fits below the lower edge of ring 50. Holder 10 can be released by applying sufficient force upwards on handle 52 to overcome the retention force of flexible tab 100. Generally, the embodiments set forth in FIGS. 1–8 are for use with implantation of annuloplasty rings or the ring component 50 of two piece valves.

Figure 9A:
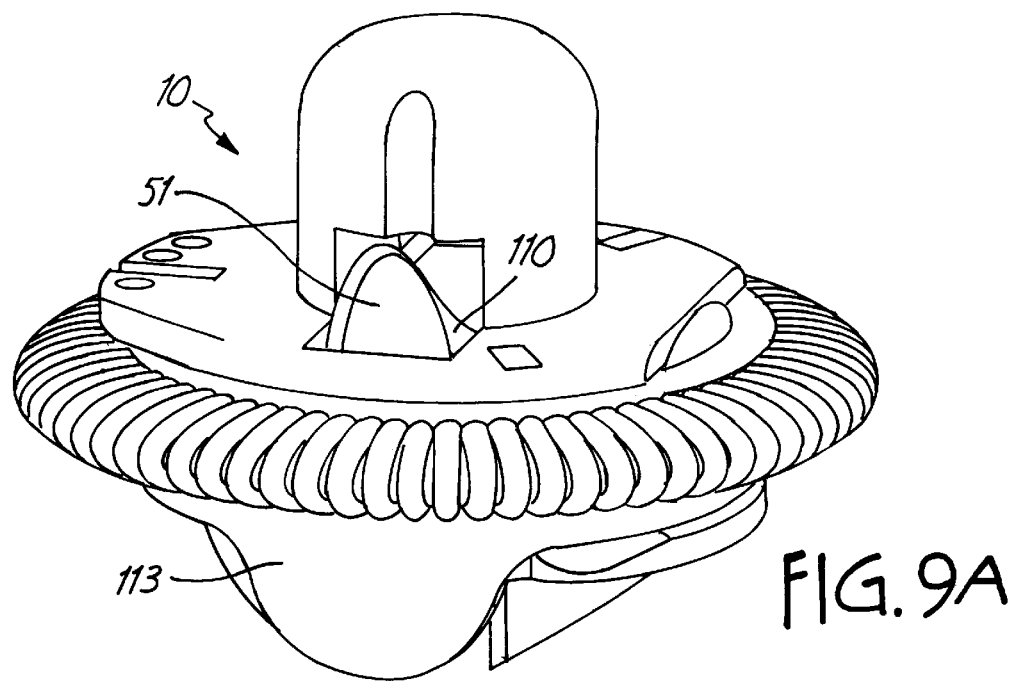
FIGS. 9A and 9B are perspective views and FIG. 9C is a side cross-sectional view of the holder in accordance with another embodiment.
Figure 9B:
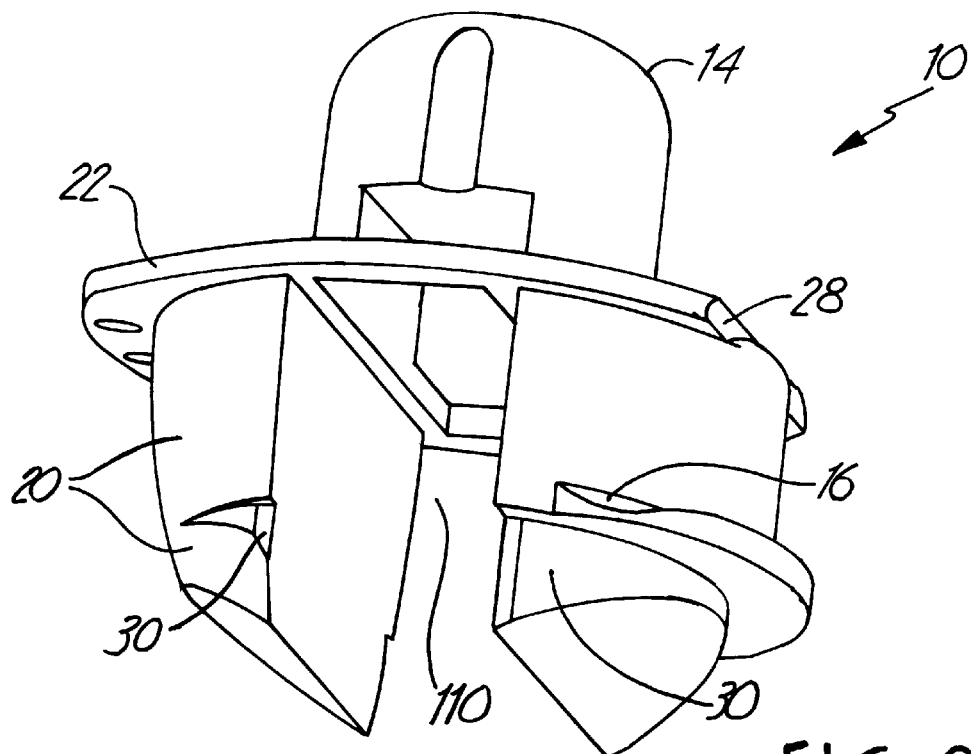
Figure 9C:
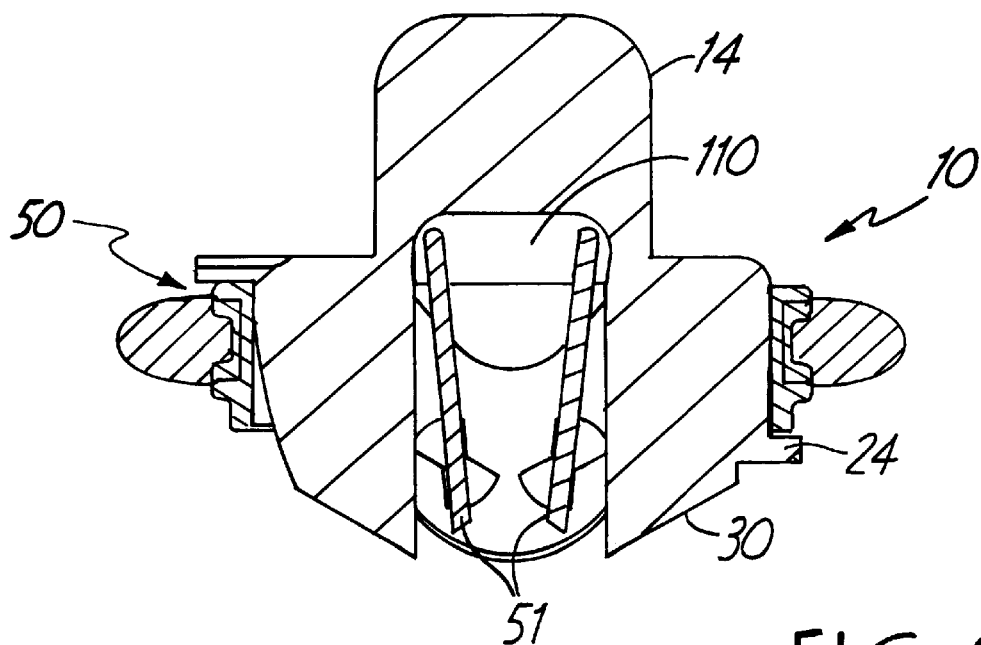

FIG. 9A is a perspective view of an aortic holder attached to a one-piece conventional mechanical heart valve. FIG. 9B is a side perspective view and FIG. 9C is a side cross-sectional view of holder 10 in accordance with another embodiment for holding a one-piece aortic valve. In the embodiment of FIGS. 9A, 9B, and 9C, cutaway section 110 is provided in holder 10 for receiving leaflets 51. Sutures, tab 100, or other retention mechanisms can be used to secure holder 10 to ring 50.

Figure 10A:
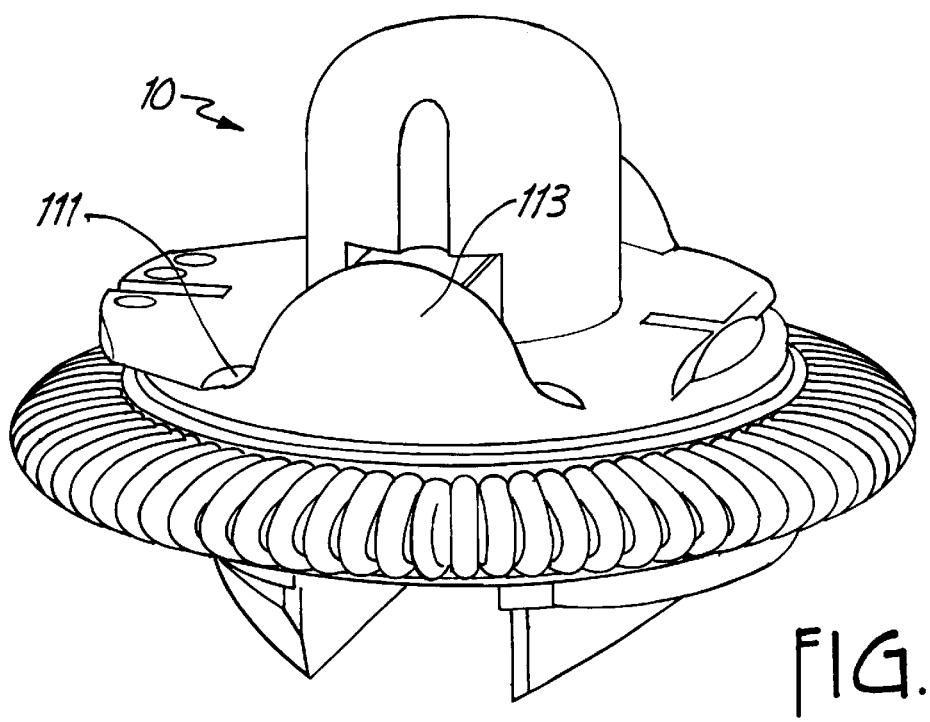
FIGS. 10A and 10B are perspective views and FIG. 10C is a side cross-sectional view of the holder in accordance with another embodiment.
Figure 10B:
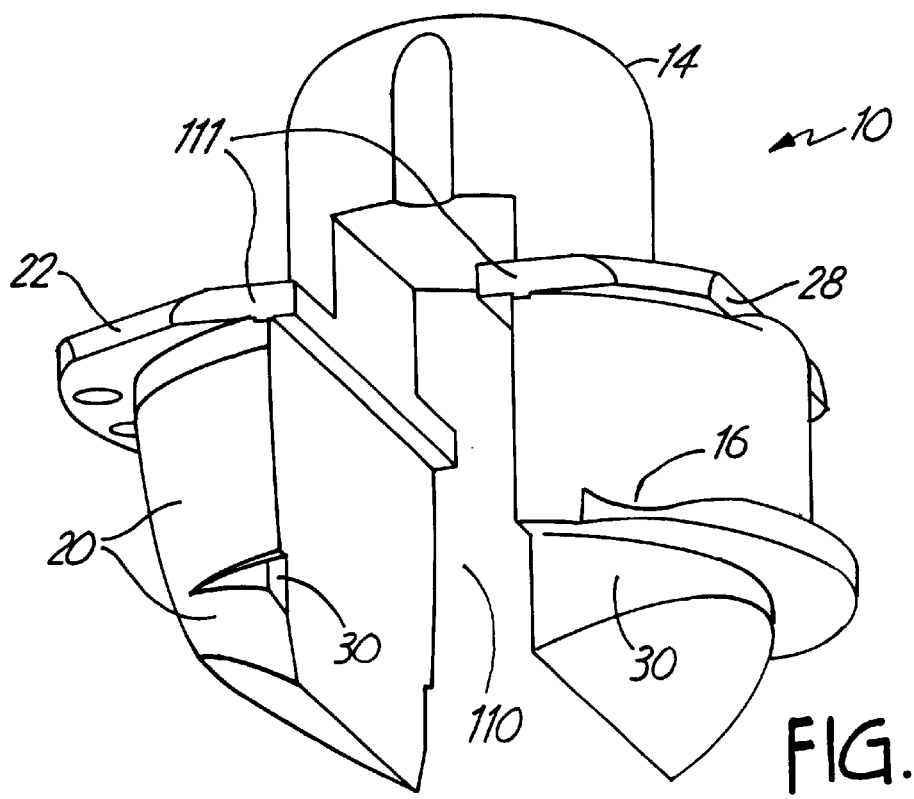
Figure 10C:
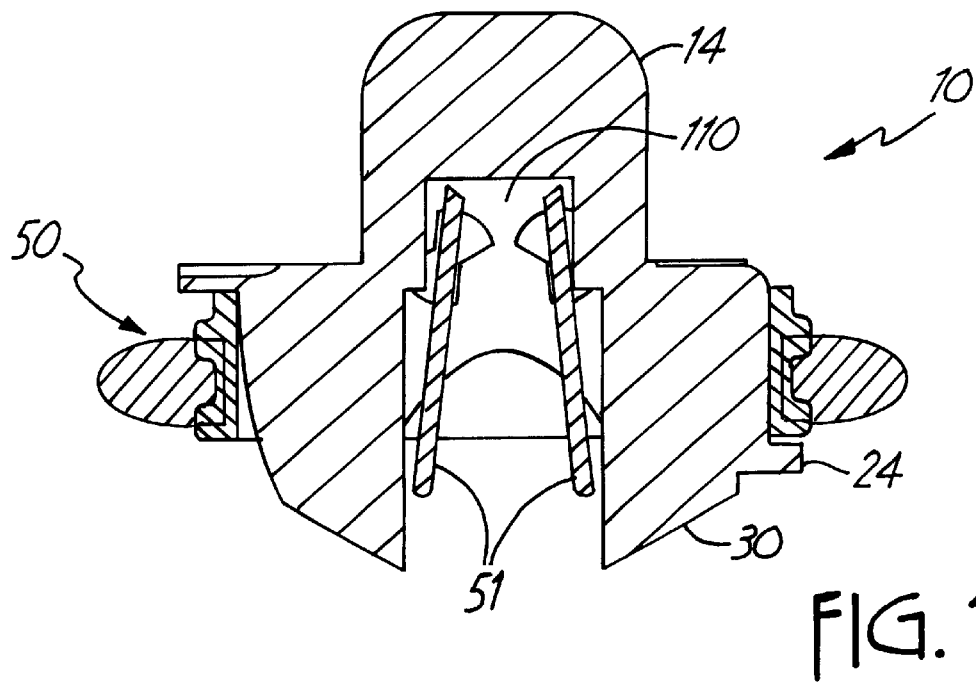

FIG. 10A is a perspective view, FIG. 10B is a side view, and FIG. 10C is a cross sectional view of holder 10 in accordance with another embodiment for holding a one-piece conventional mitral valve. In the embodiment of FIGS. 10A, 10B and 10C, cutaway section 110 is provided in holder 10 for receiving leaflets 51. Sutures, tab 100, or other retention mechanisms can be used to secure holder 10 to ring 50. Cutaway notch 111 is cut away to provide clearance for valve features such as pivot guards 113 found on the St. Jude Medical® valve.

The holder of the present invention may be formed using any appropriate techniques including molding, such as injection molding, or machining the holder, either as a single piece or as multiple pieces. The holder can be fabricated using any biocompatible material, i.e., polysulfone, polyphenylsulfone (such as Radel®), polyetheretherketone, acetal nitrile (such as Delrin®), and polytetrafluoroethylene (PTFE).

The invention provides various advantages over the prior art. For example, the invention is relatively easy to manufacture and only one suture is required for attachment. The prosthetic ring is easily released after the suture is cut by slightly lifting and tilting the holder. The holder does not require any moving parts. There is no need for two separate tools as the holder can be used both for holding a prosthetic ring and for later rotating the heart valve, if appropriate. In contrast to the design shown in U.S. Pat. No. 5,776,187, only a single suture is required to be cut. The present invention provides improved ease of manufacture and implantation.

Although the present invention has been described with reference to preferred embodiments, workers skilled in the art will recognize that changes may be made in form and detail without departing from the spirit and scope of the invention.

What is claimed is:

1. An apparatus for attaching to a prosthetic ring for implantation in a heart, comprising:
   a holder body configured to fit in the ring;
   a boss comprising at least a partial generally cylindrical portion extending around the holder body;
   a backing lip extending from a proximal end of the boss and having a diameter which is greater than a diameter of the boss;
   a shoulder tab extending from a distal end of the boss beyond a diameter of the boss configured to secure the prosthetic ring between the backing lip and the shoulder tab, the shoulder tab extending only partially around the boss; and
   a region in the boss generally opposite the shoulder tab configured to allow the boss to couple to the prosthetic ring when tilted relative to the ring.

2. The apparatus of claim 1 wherein said holder body is configured to fit in an annuloplasty ring.

3. The apparatus of claim 1 wherein said holder body is configured to be coupled to a prosthetic ring which includes a cuff of a prosthetic heart valve.

4. The apparatus of claim 1 wherein said holder body is configured to be coupled to a prosthetic ring which includes an outer ring of a two piece heart valve.

5. The apparatus of claim 3 wherein the holder body further includes a valve rotation portion configured to engage the orifice of the prosthetic heart valve.

6. The apparatus of claim 3 wherein the holder body is configured to transmit torque to a valve subassembly to thereby cause rotation relative to the cuff of the prosthetic heart valve.

7. The apparatus of claim 1 wherein the boss includes a relief area formed therein configured to allow removal from the prosthetic ring.

8. The apparatus of claim 1 wherein the backing lip includes a relief area formed therein and configured to allow the holder body to be tilted relative to the prosthetic ring to thereby separate the holder body from the prosthetic ring.

9. The apparatus of claim 1 wherein the shoulder tab includes a relief area formed therein and configured to allow the holder body to be tilted relative to the prosthetic ring to thereby separate the holder body from the prosthetic ring.

10. The apparatus of claim 1 wherein the holder body includes a handle attachment portion configured to couple to a handle.

11. The apparatus of claim 1 wherein the holder body includes markers providing visual identification of the position of the holder body.

12. The apparatus of claim 1 wherein the holder body is configured to be sutured to the prosthetic ring.

13. The apparatus of claim 12 including a channel region in the backing lip and wherein a suture extends across the channel region.

14. The apparatus of claim 12 including suture holes in the backing lip configured to receive a suture therethrough.

15. The apparatus of claim 3 wherein said holder body is configured to be coupled to a prosthetic ring which includes a cuff of a prosthetic mitral heart valve comprises a mitral heart valve.

16. The apparatus of claim 3 wherein said holder body is configured to be coupled to a prosthetic ring which includes a cuff of a prosthetic aortic heart valve comprises an aortic heart valve.

17. The apparatus of claim 1 wherein the holder body includes a cut out region formed therein for visual inspection through the holder body.

18. The apparatus of claim 1 including a lip carried on a flexible tab configured to secure the holder body to the ring.

19. The apparatus of claim 15 including a cutaway portion configured to receive leaflets of the mitral prosthetic heart valve.

20. The apparatus of claim 16 including a cutaway portion configured to receive leaflets of the aortic prosthetic heart valve.

* * * * *